US012702316B2

(12) United States Patent
Kim et al.

(10) Patent No.: US 12,702,316 B2
(45) Date of Patent: Aug. 11, 2026

(54) APPARATUS FOR MEASURING HEART RATE AND METHOD THEREOF

(71) Applicant: HONEYNAPS CO., LTD, Seoul (KR)

(72) Inventors: Myeoung Seok Kim, Seoul (KR); Young Jun Lee, Seoul (KR); Tae Kyoung Ha, Seoul (KR)

(73) Assignee: HONEYNAPS CO., LTD, Seoul (KR)

( * ) Notice: Subject to any disclaimer, the term of this patent is extended or adjusted under 35 U.S.C. 154(b) by 639 days.

(21) Appl. No.: 18/072,359

(22) Filed: Nov. 30, 2022

(65) Prior Publication Data

US 2024/0081670 A1 Mar. 14, 2024

(30) Foreign Application Priority Data

Sep. 8, 2022 (KR) ........................ 10-2022-0113949

(51) Int. Cl.
*A61B 5/024* (2006.01)
*A61B 5/00* (2006.01)
(Continued)

(52) U.S. Cl.
CPC ........ *A61B 5/02405* (2013.01); *A61B 5/1102* (2013.01); *A61B 5/725* (2013.01); *A61B 8/5223* (2013.01)

(58) Field of Classification Search
CPC ... A61B 5/02405; A61B 5/1102; A61B 5/725; A61B 8/5223
See application file for complete search history.

(56) References Cited

U.S. PATENT DOCUMENTS 8,262,582 B2 * 9/2012 Kortelainen ......... A61B 5/1102 600/527
2015/0196213 A1 7/2015 Pandia et al.
(Continued)

FOREIGN PATENT DOCUMENTS

JP 2021-535817 A 12/2021
KR 10-2150635 B1 9/2020
(Continued)

OTHER PUBLICATIONS

Communication dated Oct. 2, 2024 in Korean application No. 10-2022-0113949.

*Primary Examiner* — Amanda L Steinberg
*Assistant Examiner* — Laura Hodge
(74) *Attorney, Agent, or Firm* — Sughrue Mion, PLLC

(57) ABSTRACT

The present disclosure relates to a technique for estimating the inter-beat interval (IBI) of a ballistocardiograph (BCG) signal measured using a non-contact sensor, filtering and correcting inaccurate information in the inter-beat interval estimated through clustering, and outputting a heart rate measurement result based on the filtered and corrected inter-beat interval. According to one embodiment of the present disclosure, an apparatus for measuring a heart rate may include a signal meter for measuring a ballistocardiograph (BCG) signal from a heart rate measurement target; an inter-beat interval estimator for estimating an inter-beat interval (IBI) by applying a window to the measured BCG signal; a first filter for determining a confidence value for the probability values of the estimated inter-beat interval, filtering the estimated inter-beat interval by comparing the determined confidence value with a first threshold value, and determining a first estimated value; a second filter for determining a repetition degree indicating that identical beat values are successively estimated for the estimated inter-beat interval, filtering the estimated inter-beat interval by
(Continued)

comparing the determined repetition degree with a second threshold value, and determining a second estimated value; and a heart rate output device for determining a third estimated value for the estimated inter-beat interval based on the determined first and second estimated values and outputting a heart rate based on the determined third estimated value.

8 Claims, 8 Drawing Sheets

(51) Int. Cl.
*A61B 5/11* (2006.01)
*A61B 8/00* (2006.01)

(56) References Cited

U.S. PATENT DOCUMENTS

| | | | | |
|---|---|---|---|---|
| 2018/0279956 | A1* | 10/2018 | Waydo | A61B 5/7235 |
| 2020/0268266 | A1* | 8/2020 | Majava | A61B 5/02438 |
| 2021/0228108 | A1 | 7/2021 | Kinnunen et al. | |
| 2021/0298683 | A1* | 9/2021 | Jung | G01G 19/445 |

FOREIGN PATENT DOCUMENTS

| | | | | |
|---|---|---|---|---|
| KR | 10-2387703 B1 | | 4/2022 | |
| WO | WO-2015127193 A1 | * | 8/2015 | A61B 5/02405 |

* cited by examiner

【FIG. 1】
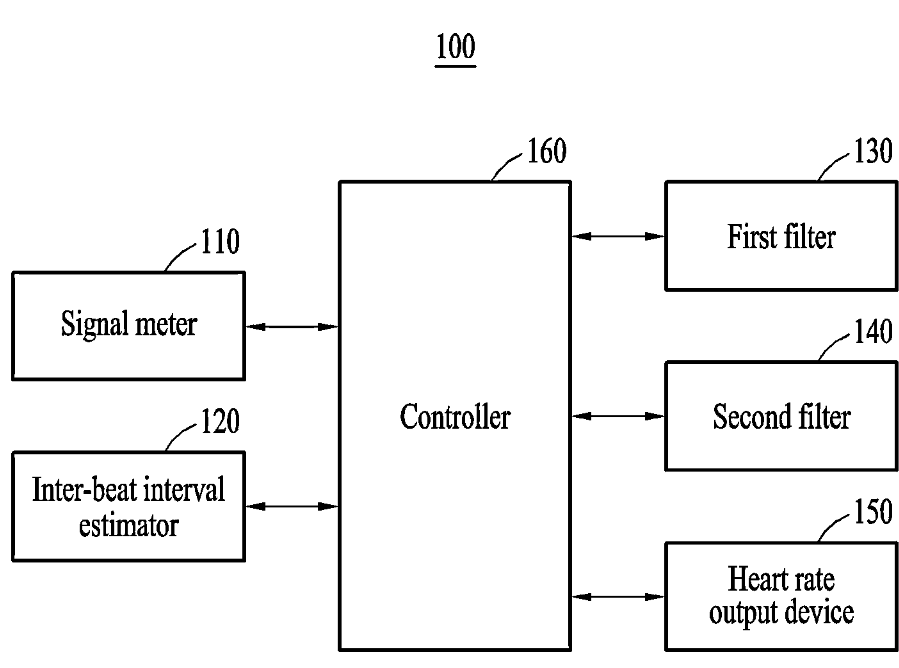

【FIG. 2】
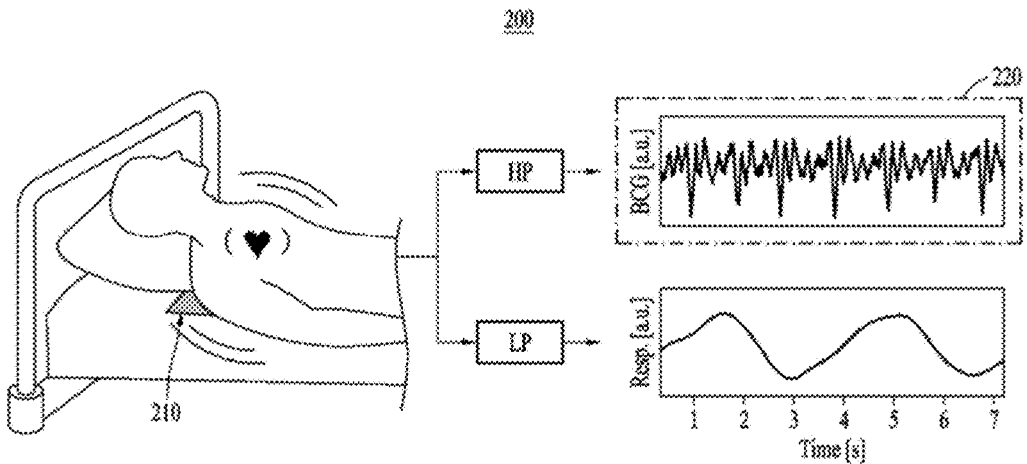

【FIG. 3】
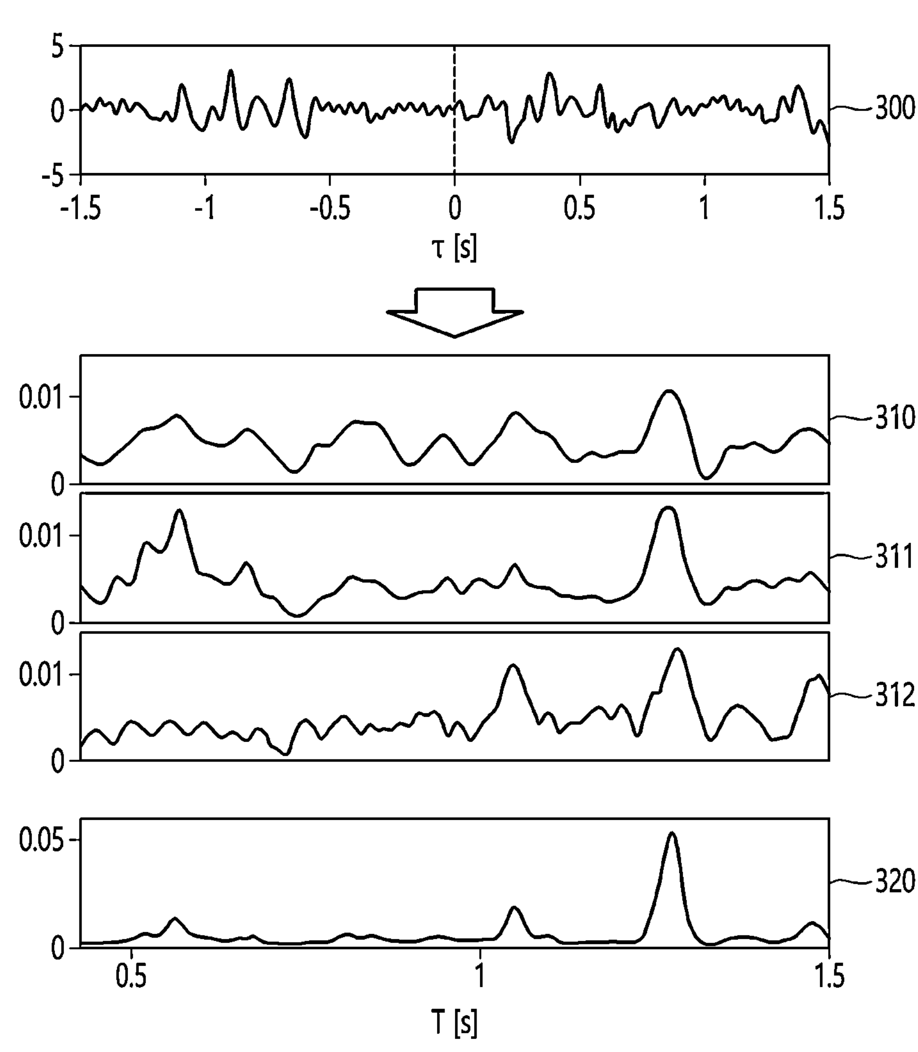

【FIG. 4】
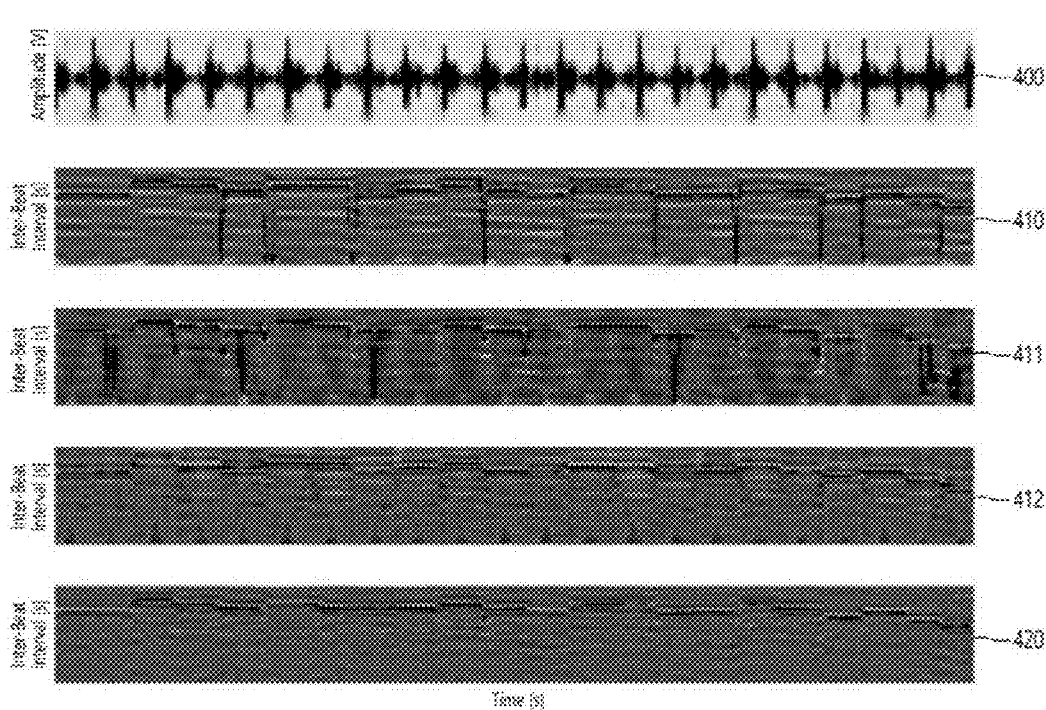

【FIG. 5A】
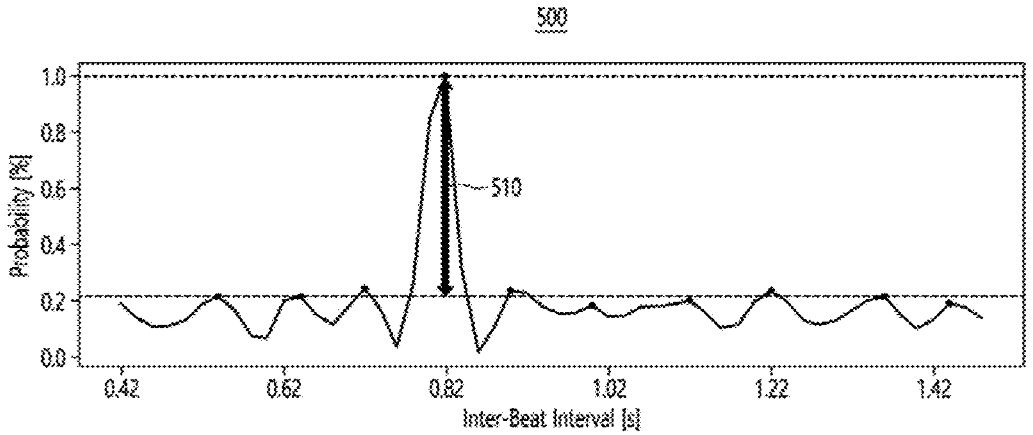

【FIG. 5B】
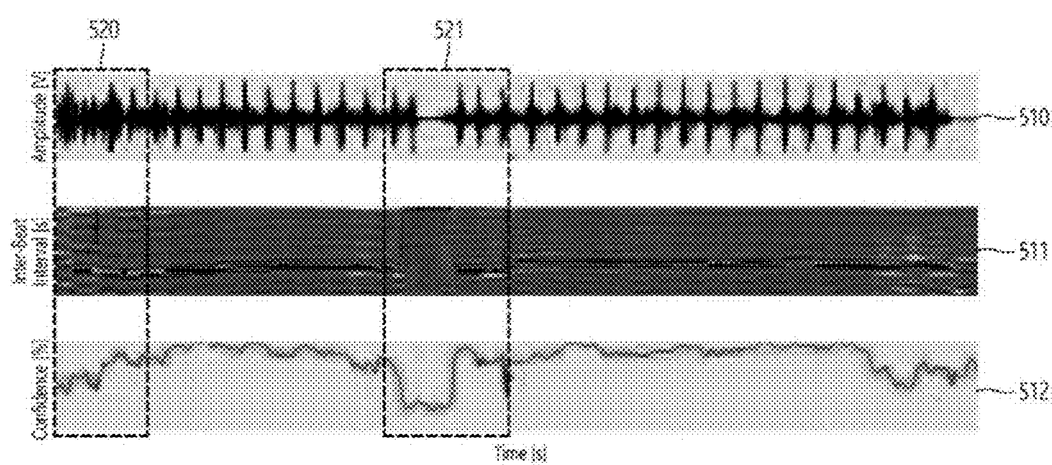

【FIG. 6】
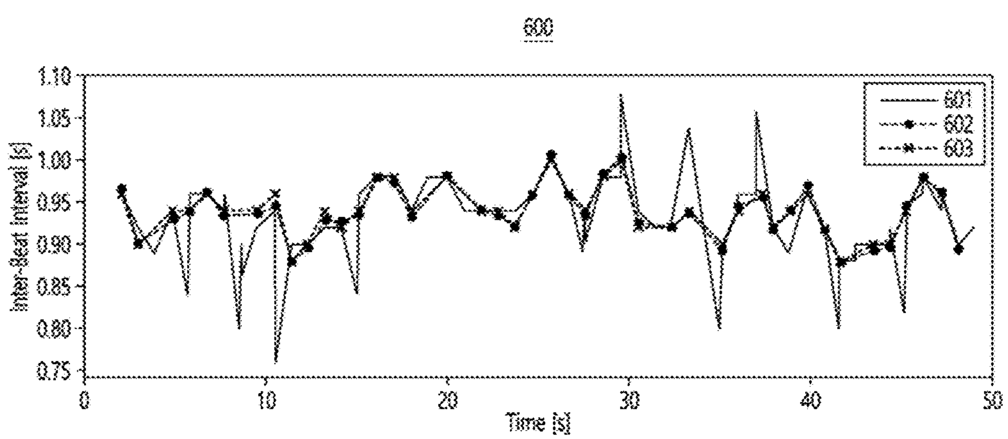

【FIG. 7】
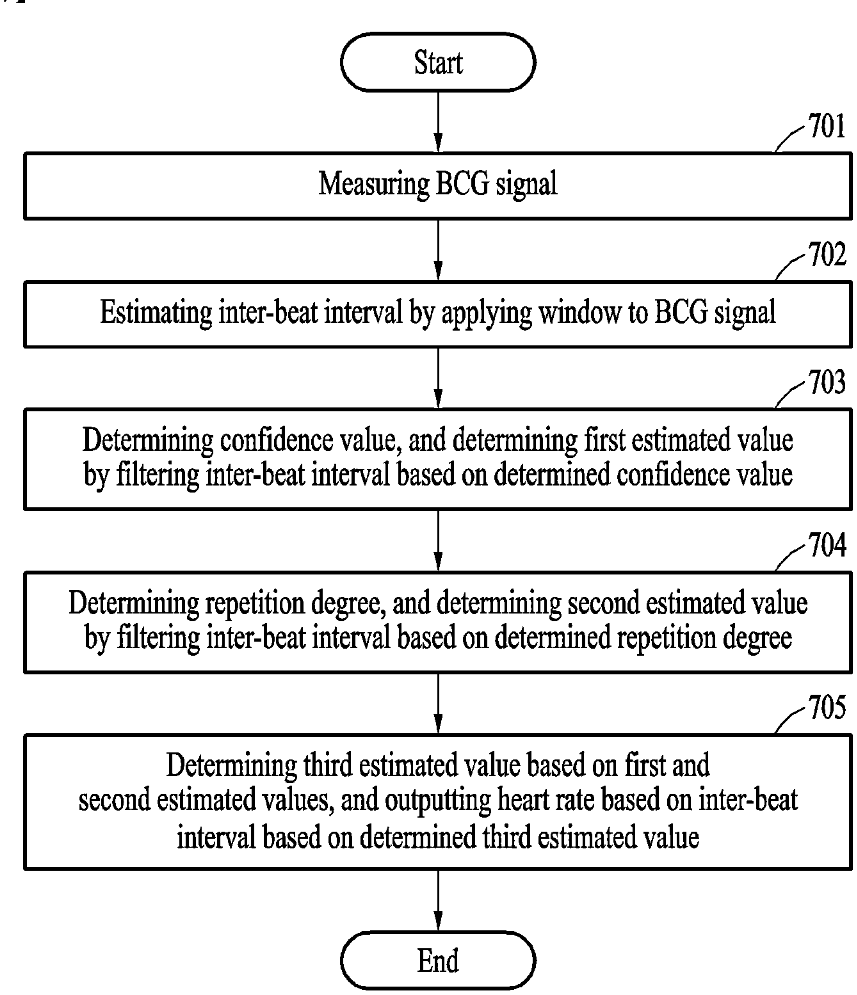

APPARATUS FOR MEASURING HEART RATE AND METHOD THEREOF

This study was supported by Institute for Information & communication Technology Planning & evaluation (IITP) grant funded by Ministry of Science and ICT (MIST) [2021-0-01521, Development of Patient-Specific Cognitive Behavioral Therapy (CBT-I) Digital Treatment Technology to Improve Insomnia].

CROSS-REFERENCE TO RELATED APPLICATION

This application claims priority to Korean Patent Application No. 10-2022-0113949, filed on Sep. 8, 2022, in the Korean Intellectual Property Office, the disclosure of which is incorporated herein by reference.

STATEMENT REGARDING SPONSORED RESEARCH OR DEVELOPMENT

This present invention was developed through the Seoul Economic Promotion Agency (2023 Bio and Medical Technology Commercialization Support Project) (BT230157) (Development of a diagnostic solution for heart disease and brain neurological disorders based on sleep polysomnography data).

BACKGROUND OF THE DISCLOSURE

Field of the Disclosure

The present disclosure relates to an apparatus for measuring a heart rate and a method thereof. More particularly, the present disclosure relates to a technique for estimating the inter-beat interval (IBI) of a ballistocardiograph (BCG) signal measured using a non-contact sensor, filtering and correcting inaccurate information in the inter-beat interval estimated through clustering, and outputting a heart rate measurement result based on the filtered and corrected inter-beat interval.

Description of the Related Art

A heart rate is a basic indicator of the condition of the human body. Accordingly, it is important to measure a heart rate consistently, reliably, and accurately.

A heart rate may be measured by a contact-type measurement method or a non-contact-type measurement method.

Electrocardiogram (ECG), which is a contact-type measurement method, can measure a heart rate consistently, reliably, and accurately, but has limitations in measuring a heart rate in various environments due to limitations of a touch sensor.

Accordingly, a method of measuring a heart rate using a non-contact sensor such as a polyvinylidene fluoride (PVDF) sensor, a radar sensor, and a camera has been intensively studied.

Thereamong, the PVDF sensor is installed in a non-contact manner at the bottom of a place (bed or chair) where a measurement target or user is located, measures ballistocardiograph (BCG), and measures a heart rate based on the J-peak of the measured BCG.

However, the non-contact sensor is susceptible to noise generated in external environments, and the noise makes it difficult to accurately measure a heart rate.

SUMMARY OF THE DISCLOSURE

Therefore, the present disclosure has been made in view of the above problems, and it is an object of the present disclosure to provide a heart rate measurement apparatus for estimating the inter-beat interval (IBI) of a ballistocardiograph (BCG) signal measured using a non-contact sensor, filtering and correcting inaccurate information in the inter-beat interval estimated through clustering, and outputting a heart rate measurement result based on the filtered and corrected inter-beat interval and a heart rate measurement method thereof.

It is another object of the present disclosure to increase heart rate measurement accuracy and secure the convenience of a user using a non-contact sensor by determining a confidence value and a repetition degree from an inter-beat interval estimated from a BCG signal and filtering and correcting unnecessary information corresponding to noise by comparing the determined confidence value and repetition degree with threshold values.

It is yet another object of the present disclosure to provide accurate heart rate measurement results under various environments based on a non-contact sensor by filtering and correcting inter-beat intervals estimated from BCG signals using a confidence value and a repetition degree.

In accordance with one aspect of the present disclosure, provided is an apparatus for measuring a heart rate including a signal meter for measuring a ballistocardiograph (BCG) signal from a heart rate measurement target; an inter-beat interval estimator for estimating an inter-beat interval (IBI) by applying a window to the measured BCG signal; a first filter for determining a confidence value for probability values of the estimated inter-beat interval, filtering the estimated inter-beat interval by comparing the determined confidence value with a first threshold value, and determining a first estimated value; a second filter for determining a repetition degree indicating that identical beat values are successively estimated for the estimated inter-beat interval, filtering the estimated inter-beat interval by comparing the determined repetition degree with a second threshold value, and determining a second estimated value; and a heart rate output device for determining a third estimated value for the estimated inter-beat interval based on the determined first and second estimated values and outputting a heart rate based on the determined third estimated value.

The first filter may determine the confidence value based on a difference between a maximum probability peak value among the probability values and an average value of other peak values.

When the confidence value exceeds the first threshold value, the first filter may determine the first estimated value from the estimated inter-beat interval. When the confidence value is less than or equal to the first threshold value, the first filter may estimate the estimated inter-beat interval as noise and exclude the estimated inter-beat interval.

The second filter may determine the repetition degree by configuring a set of values in which the identical beat values are successively repeated for a preset time.

When the repetition degree determined from the estimated inter-beat interval is greater than or equal to the second threshold value, the second filter may determine the second estimated value from the estimated inter-beat interval. When the repetition degree determined from the estimated inter-beat interval is less than the second threshold value, the second filter may estimate the estimated inter-beat interval as noise and exclude the estimated inter-beat interval.

The heart rate output device may output an inter-beat interval corresponding to the third filtering value satisfying that the confidence value exceeds the first threshold value based on the first filtering value in the estimated inter-beat interval and the repetition degree is greater than or equal to the second threshold value based on the second filtering value, and may convert the output inter-beat interval into a heart rate and output the converted heart rate.

The inter-beat interval estimator may estimate an autocorrelation estimate, an average magnitude difference function (AMDF) estimate, and a maximum amplitude pair (MAP) estimate from the BCG signal, may combine peaks of probability density functions of the estimated auto-correlation estimate, average magnitude difference function estimate, and maximum amplitude pair estimate to determine a probabilistic fusion estimate, and may estimate the inter-beat interval based on a peak of a probability density function of the probabilistic fusion estimate.

The inter-beat interval estimator may estimate the autocorrelation estimate while a probability value is changed based on autocorrelation on a right side of a portion designated as the window and a left side of the portion designated as the window, may estimate the average magnitude difference function estimate by taking a reciprocal number of a probability value according to a difference between the right side of the portion designated as the window and the left side of the portion designated as the window, and may estimate the maximum amplitude pair estimate as a probability value when two peaks exist in a section spaced apart by a window size from the portion designated as the window.

In accordance with another aspect of the present disclosure, provided is a method of measuring a heart rate including measuring a ballistocardiograph (BCG) signal from a heart rate measurement target by a signal meter; estimating, by an inter-beat interval estimator, an inter-beat interval (IBI) by applying a window to the measured BCG signal; by a first filter, determining a confidence value for probability values of the estimated inter-beat interval, filtering the estimated inter-beat interval by comparing the determined confidence value with a first threshold value, and determining a first estimated value; by a second filter, determining a repetition degree indicating that identical beat values are successively estimated for the estimated inter-beat interval, filtering the estimated inter-beat interval by comparing the determined repetition degree with a second threshold value, and determining a second estimated value; and by a heart rate output device, determining a third estimated value for the estimated inter-beat interval based on the determined first and second estimated values and outputting a heart rate based on the determined third estimated value.

The determining of a first estimated value may include, by the first filter, determining the confidence value based on a difference between a maximum probability peak value among the probability values and an average value of other peak values; determining the first estimated value from the estimated inter-beat interval when the confidence value exceeds the first threshold value; and estimating the estimated inter-beat interval as noise and excluding the estimated inter-beat interval when the confidence value is less than or equal to the first threshold value.

The determining of a second estimated value may include determining the repetition degree by configuring a set of values in which the identical beat values are successively repeated for a preset time; determining the second estimated value from the estimated inter-beat interval when the repetition degree determined from the estimated inter-beat interval is greater than or equal to the second threshold value; and estimating the estimated inter-beat interval as noise and excluding the estimated inter-beat interval when the repetition degree determined from the estimated inter-beat interval is less than the second threshold value.

The outputting of a heart rate may include outputting an inter-beat interval corresponding to the third filtering value satisfying that the confidence value exceeds the first threshold value based on the first filtering value in the estimated inter-beat interval and the repetition degree is greater than or equal to the second threshold value based on the second filtering value, and converting the output inter-beat interval into a heart rate and outputting the converted heart rate.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 is a block diagram for explaining an apparatus for measuring a heart rate according to one embodiment of the present disclosure;

FIG. 2 shows a situation in which a signal is measured by the signal meter of an apparatus for measuring a heart rate according to one embodiment of the present disclosure;

FIGS. 3 and 4 are diagrams for explaining an inter-beat interval estimated by an inter-beat interval estimator according to one embodiment of the present disclosure;

FIGS. 5A and 5B are diagrams for explaining operation of a first filter according to one embodiment of the present disclosure;

FIG. 6 is a graph showing the accuracy of a heart rate measurement result measured by an apparatus for measuring a heart rate according to one embodiment of the present disclosure; and FIG. 7 is a flowchart for explaining a method of measuring a heart rate according to one embodiment of the present disclosure.

DETAILED DESCRIPTION OF THE DISCLOSURE

Hereinafter, the embodiments of the present disclosure will be described in detail with reference to the drawings.

However, it should be understood that the present disclosure is not limited to the embodiments according to the concept of the present disclosure, but includes changes, equivalents, or alternatives falling within the spirit and scope of the present disclosure.

In the following description of the present disclosure, detailed description of known functions and configurations incorporated herein will be omitted when it may make the subject matter of the present disclosure unclear.

In addition, the terms used in the specification are defined in consideration of functions used in the present disclosure, and can be changed according to the intent or conventionally used methods of clients, operators, and users. Accordingly, definitions of the terms should be understood on the basis of the entire description of the present specification.

In description of the drawings, like reference numerals may be used for similar elements.

The singular expressions in the present specification may encompass plural expressions unless clearly specified otherwise in context.

In this specification, expressions such as "A or B" and "at least one of A and/or B" may include all possible combinations of the items listed together.

Expressions such as “first” and “second” may be used to qualify the elements irrespective of order or importance, and are used to distinguish one element from another and do not limit the elements.

It will be understood that when an element (e.g., first) is referred to as being “connected to” or “coupled to” another element (e.g., second), it may be directly connected or coupled to the other element or an intervening element (e.g., third) may be present.

As used herein, “configured to” may be used interchangeably with, for example, “suitable for”, “ability to”, “changed to”, “made to”, “capable of”, or “designed to” in terms of hardware or software.

In some situations, the expression “device configured to” may mean that the device “may do ~” with other devices or components.

For example, in the sentence “processor configured to perform A, B, and C”, the processor may refer to a general purpose processor (e.g., CPU or application processor) capable of performing corresponding operation by running a dedicated processor (e.g., embedded processor) for performing the corresponding operation, or one or more software programs stored in a memory device.

In addition, the expression “or” means “inclusive or” rather than “exclusive or”.

That is, unless mentioned otherwise or clearly inferred from context, the expression “x uses a or b” means any one of natural inclusive permutations.

Terms, such as “unit” or “module”, etc., should be understood as a unit that processes at least one function or operation and that may be embodied in a hardware manner, a software manner, or a combination of the hardware manner and the software manner.

FIG. 1 is a block diagram for explaining an apparatus for measuring a heart rate according to one embodiment of the present disclosure.

FIG. 1 shows an example of components of the apparatus for measuring a heart rate according to one embodiment of the present disclosure.

Referring to FIG. 1, an apparatus 100 for measuring a heart rate according to one embodiment of the present disclosure includes a signal meter 110, an inter-beat interval estimator 120, a first filter 130, a second filter 140, and a heart rate output device 150.

A controller 160 controls operation of the signal meter 110, the inter-beat interval estimator 120, the first filter 130, the second filter 140, and the heart rate output device 150.

According to one embodiment of the present disclosure, the signal meter 110 may measure a ballistocardiograph (BCG) signal from a heart rate measurement target.

For example, the signal meter 110 is a non-contact sensor, and may obtain a BCG signal without directly contacting a heart rate measurement target.

According to one embodiment of the present disclosure, the inter-beat interval estimator 120 may estimate an inter-beat interval by applying a window to the waveform of a BCG signal over time.

For example, the inter-beat interval estimator 120 may estimate an auto-correlation estimate, an average magnitude difference function (AMDF) estimate, and a maximum amplitude pair (MAP) estimate from a BCG signal.

In addition, the inter-beat interval estimator 120 may combine the peaks of the probability density functions of an estimated auto-correlation estimate, average magnitude difference function estimate, and maximum amplitude pair estimate to determine a probabilistic fusion estimate.

In addition, the inter-beat interval estimator 120 may estimate an inter-beat interval based on the peak of the probability density function of a probabilistic fusion estimate.

For example, the inter-beat interval may be an interval between the peaks of beats, and may be an RR interval indicating a heart rate when divided by 60 seconds.

For example, the inter-beat interval estimator 120 may estimate an auto-correlation estimate while a probability value is changed based on autocorrelation on the right side of a portion designated as a window and the left side of the portion designated as the window.

The inter-beat interval estimator 120 may estimate an average magnitude difference function estimate by taking the reciprocal number of a probability value according to a difference between the right side of a portion designated as a window and the left side of the portion designated as the window.

The inter-beat interval estimator 120 may estimate a maximum amplitude pair estimate as a probability value when two peaks exist in a section spaced apart by a window size from a portion designated as a window.

For example, the inter-beat interval estimator 120 may perform inter-beat interval estimation based on auto-correlation, an average magnitude difference function, a maximum amplitude pair, and a Bayesian probability approach to successively estimate an inter-beat interval.

According to one embodiment of the present disclosure, the first filter 130 may determine a confidence value for the probability values of an inter-beat interval estimated by the inter-beat interval estimator 120, may filter the estimated inter-beat interval by comparing the determined confidence value and a first threshold value, and may determine a first estimated value.

For example, the first filter 130 may determine the confidence value based on a difference between a maximum probability peak value among the probability values and an average value of other peak values.

For example, the inter-beat interval is a value of a probability density function, and may be expressed as a probability value.

According to one embodiment of the present disclosure, when the confidence value exceeds the first threshold value, the first filter 130 may determine the first estimated value from the estimated inter-beat interval. When the confidence value is less than or equal to the first threshold value, the first filter 130 may estimate the estimated inter-beat interval as noise and exclude the estimated inter-beat interval.

That is, when the confidence value exceeds the first threshold value, the first filter 130 determines an inter-beat interval corresponding to the confidence value as a first estimated value accurately estimated without noise. When the confidence value is less than or equal to the first threshold value, the first filter 130 estimates an inter-beat interval as noise and excludes the inter-beat interval.

That is, the first filter 130 may cluster only inter-beat intervals exceeding the confidence value and filter the inter-beat intervals as the first estimated value.

For example, the first threshold value may be a reference value for discriminating noise and non-noise values in comparison with a confidence value.

For example, the controller 160 may collect BCG data and ECG data for the same heart rate measurement target, determine a value at which both data fluctuate according to a degree to which noise is input, and determine a first threshold value using the determined value.

According to one embodiment of the present disclosure, the second filter 140 determines a repetition degree indicating that identical beat values are successively estimated for an inter-beat interval estimated by the inter-beat interval estimator 120.

In addition, the second filter 140 compares a predetermined repetition degree with a second threshold value and filters an estimated inter-beat interval to determine a second estimated value.

For example, the second threshold value related to the number of times the predetermined repetition degree repeatedly appears within one window.

According to one embodiment of the present disclosure, the second filter 140 may determine a repetition degree by configuring a set of values in which identical beat values are successively repeated for a preset time.

For example, when a repetition degree determined from an estimated inter-beat interval is greater than or equal to a second threshold value, the second filter 140 may determine a second estimated value from the estimated inter-beat interval. When a repetition degree determined from an estimated inter-beat interval is less than a second threshold value, the second filter 140 may estimate the estimated inter-beat interval as noise and exclude the estimated inter-beat interval.

Since the inter-beat interval is repeated for a preset time ($\Delta t$) and successively estimated, when a correct value is estimated, identical values should be successively estimated.

The repetition degree may indicate to what extent identical estimates are estimated successively.

According to one embodiment of the present disclosure, the second filter 140 configures successively repeated values as a specific set, and calculates the number of repetitions for each estimate value at each time point.

Accordingly, when a repetition degree is n times or more, which is a second threshold value, the second filter 140 determines the pre-estimated inter-beat interval as a correct estimate. When the above condition is not satisfied, the second filter 140 determines the pre-estimated inter-beat interval as noise corresponding to an incorrect estimated value and excludes the pre-estimated inter-beat interval.

That is, the second filter 140 determines a second estimated value by clustering only inter-beat intervals having a repetition degree greater than or equal to a second threshold value.

According to one embodiment of the present disclosure, the heart rate output device 150 may determine a third estimated value based on the first estimated value and the second estimated value, and may output a heart rate based on the determined third estimated value.

For example, the heart rate output device 150 may filter and output only inter-beat intervals corresponding to a third filtering value satisfying that a confidence value exceeds a first threshold value based on a first filtering value in an inter-beat interval estimated by the inter-beat interval estimator 120, and a repetition degree is greater than or equal to a second threshold value based on a second filtering value. The heart rate output device 150 may convert the output inter-beat interval into a heart rate and output the converted heart rate.

That is, when the confidence value exceeds the first threshold value, and the repetition degree is greater than or equal to the second threshold value, the heart rate output device 150 may determine the third filtering value and output only an inter-beat interval corresponding to the third filtering value as a reasonable estimated value.

In addition, when the confidence value is less than or equal to the first threshold value, and the repetition degree is less than the second threshold value, the heart rate output device 150 excludes the corresponding inter-beat interval. At this time, when the length of the excluded section is less than 1 second, the heart rate output device 150 interpolates. When the length of the excluded section is greater than or equal to 1 second, the heart rate output device 150 determines that the inter-beat interval is not estimated and outputs the inter-beat interval.

According to one embodiment of the present disclosure, the apparatus 100 for measuring a heart rate estimates a continuous estimate of an inter-beat interval. The apparatus 100 may apply a clustering algorithm through the first filter 130 and the second filter 140 to filter and correct inaccurate information according to the noise level of a signal.

Therefore, the present disclosure may provide a heart rate measurement apparatus for estimating the inter-beat interval (IBI) of a ballistocardiograph (BCG) signal measured using a non-contact sensor, filtering and correcting inaccurate information in the inter-beat interval estimated through clustering, and outputting a heart rate measurement result based on the filtered and corrected inter-beat interval and a heart rate measurement method thereof.

FIG. 2 shows a situation in which a signal is measured by the signal meter of an apparatus for measuring a heart rate according to one embodiment of the present disclosure.

FIG. 2 illustrates an environment in which an apparatus for measuring a heart rate according to one embodiment of the present disclosure measures a ballistocardiograph (BCG) signal using a non-contact sensor.

Referring to FIG. 2, in an environment 200 for measuring a signal according to one embodiment of the present disclosure, a measurement target is lying or sitting on a bed, and data related to a heart rate and respiration is collected through a non-contact sensor 210 located on the lower surface of the bed.

The non-contact sensor 210 outputs data related to a heart rate as a BCG signal 220. The BCG signal may be utilized as data capable of providing a heart rate measurement result based on an inter-beat interval that is an interval between beats.

That is, in the environment 200 for measuring a signal according to one embodiment of the present disclosure, the non-contact sensor 210 corresponding to a signal meter may measure a BCG signal.

FIGS. 3 and 4 are diagrams for explaining an inter-beat interval estimated by an inter-beat interval estimator according to one embodiment of the present disclosure.

FIG. 3 illustrates a procedure for estimating an inter-beat interval for a BCG signal measured in FIG. 2 by an inter-beat interval estimator according to one embodiment of the present disclosure.

Referring to FIG. 3, the inter-beat interval estimator selects a section 300 for estimating an inter-beat interval by applying a window to a BCG signal.

The inter-beat interval estimator independently outputs an auto-correlation estimate 310, an average magnitude difference function estimate 311, and a maximum amplitude pair estimate 312 for the section 300, and determines a probabilistic fusion estimate 320 by combining the independently output estimates based on a maximum amplitude pair and a Bayesian probability approach.

The auto-correlation estimate 310 is an estimate that calculates all individual delays to estimate a heart rate interval.

The average magnitude difference function estimate 311 may calculate a discrete delay such as auto-correlation with an average magnitude difference function often used for pitch tracking.

When the waveforms of BCG signals are similar, the maximum amplitude pair estimate 312 should also be small.

Thus, the reciprocal number of the maximum amplitude pair estimate 312 may be used to take a larger value for the most probable interval.

Since noise characteristics are different between the output of the auto-correlation estimate 310 and the output of the maximum amplitude pair estimate 312, the result of the maximum amplitude pair estimate 312 may have a complementary relationship with the result of an autocorrelation.

The maximum amplitude pair estimate 312 may be an estimate used for indirect peak detection using amplitude information of a signal.

For example, the auto-correlation estimate 310 may be estimated while a probability value is changed based on autocorrelation on the right side of a portion designated as a window and the left side of the portion designated as the window.

The average magnitude difference function estimate 311 may be estimated by taking the reciprocal number of a probability value according to a difference between the right side of a portion designated as a window and the left side of the portion designated as the window.

The maximum amplitude pair estimate 312 may be estimated as a probability value when two peaks exist in a section separated by a window size from a portion designated as a window.

For example, the probabilistic fusion estimate 320 may be estimated by combining the peak values of the auto-correlation estimate 310, the average magnitude difference function estimate 311, and the maximum amplitude pair estimate 312.

FIG. 4 shows data obtained by estimating an inter-beat interval for a BCG signal measured in FIG. 2 by the inter-beat interval estimator according to one embodiment of the present disclosure.

Referring to FIG. 4, a BCG signal 400, an auto-correlation estimate 410, an average magnitude difference function estimate 411, a maximum amplitude pair estimate 412, and a probabilistic fusion estimate 420 are exemplified.

In each graph, the horizontal axis represents the passage of time, and the vertical axis represents the change of each value.

For example, the BCG signal 400 may be input data obtained by filtering measurement data of a PVDF sensor.

The auto-correlation estimate 410, the average magnitude difference function estimate 411, and the maximum amplitude pair estimate 412 may be a set of probability density functions over time of each estimation result.

The probabilistic fusion estimate 420 may be an inter-beat interval as the final result of probability fusion.

FIGS. 5A and 5B are diagrams for explaining operation of a first filter according to one embodiment of the present disclosure.

FIGS. 5A and 5B show a confidence value determined by the first filter according to one embodiment of the present disclosure.

Referring to a graph 500 of FIG. 5A, the horizontal axis represents change in inter-beat intervals, the vertical axis represents probability values, and a confidence value 510 is shown.

The confidence value 510 may be modeled as the difference between a peak value (largest probability peak) of the maximum probability of a probabilistic fusion estimate and an average value of other probability peaks.

That is, the confidence value 510 is for selecting and excluding inter-beat intervals with low reliability, and may be determined by excluding an average value of the peaks of the remaining probability from the highest probability peak.

The confidence value 510 may be used to filter out and correct for inaccurate information in inter-beat intervals.

That is, an inter-beat interval value may be determined by performing filtering, such as clustering, on the most estimated inter-beat interval value in a clustered set.

For example, a peak (Pi) of a probability fusion result in relation to second filtering that applies a repetition degree, a time index (Ti) at which Pi is estimated, a set (Pj) of consecutively repeating P sets, a T set (Tj) mapped to the P set, repeated estimates (var(Pj)), and the number (n Pj) of repetition of Pj are set as variables.

When Pi is accurately estimated in a sliding window, P, which is an inter-beat interval estimated from probability fusion, should be repeated with the same result, showing the characteristic of temporal locality.

When a set of repeated values is small, this set should be ignored, and the position of the corresponding BCG peak may be estimated through Tj.

To accurately estimate an inter-beat interval, when (n Pj) is less than a second threshold value, the corresponding estimated value (var(Pj)) is ignored.

Based on the above-described conditions, second filtering may be performed based on the repetition degree.

FIG. 5B illustrates that inaccurate information is classified based on a confidence value determined by a first filter according to one embodiment of the present disclosure.

Referring to FIG. 5B, a BCG signal 510, a probabilistic fusion estimate 511, and a confidence value 512 are arranged according to the same time.

A first section 520 and a second section 521 are exemplified. The first section 520 is a section that has no noise and is filtered as an inter-beat interval for measuring a heart rate, and the second section 521 is a section having noise.

In the first section 520, the confidence value increases. In the second section 521, the confidence value decreases.

That is, filtering may be performed by clustering the second section 521 that is a section in which noise is present and the first section 520 that is a section in which noise is not present based on a confidence value.

FIG. 6 is a graph showing the accuracy of a heart rate measurement result measured by an apparatus for measuring a heart rate according to one embodiment of the present disclosure.

Referring to FIG. 6, the accuracy of the heart rate measurement result of an apparatus for measuring a heart rate according to one embodiment of the present disclosure is compared with an ECG signal based on the prior art and a touch sensor.

In a graph 600 of FIG. 6, the horizontal axis represents the passage of time, and the vertical axis represents inter-beat intervals.

The leader line 601 indicates the result of estimating an inter-beat interval using a BCG signal based on the prior art, the leader line 602 indicates the result of outputting an inter-beat interval as a third filtering value as a final output by applying first filtering and second filtering to an inter-beat interval estimated from a BCG signal according to one embodiment of the present disclosure, and the leader line 603 indicates the inter-beat interval of an ECG signal.

Since an ECG signal uses a touch sensor, compared to a BCG signal, the ECG signal is resistant to noise. In addition, the ECG signal may measure a heart rate more accurately.

That is, an inter-beat interval similar to an ECG signal may represent an inter-beat interval estimate resistant to noise.

When the leader line 601 and the leader line 603 are compared, there is a difference in the inter-beat interval.

This indicates that a relatively large amount of noise is present in an inter-beat interval based on the leader line 601.

On the other hand, when the leader line 602 and the leader line 603 are compared, the lines exhibit similar inter-beat intervals.

That is, the leader line 602 may be an inter-beat interval estimate in a state in which noise is relatively heavily filtered.

Accordingly, the present disclosure may increase heart rate measurement accuracy and secure the convenience of a user using a non-contact sensor by determining a confidence value and a repetition degree from an inter-beat interval estimated from a BCG signal and filtering and correcting unnecessary information corresponding to noise by comparing the determined confidence value and repetition degree with threshold values.

FIG. 7 is a flowchart for explaining a method of measuring a heart rate according to one embodiment of the present disclosure.

According to the method of measuring a heart rate shown in FIG. 7, an inter-beat interval of a ballistocardiograph (BCG) signal measured by a non-contact sensor is estimated, the estimated inter-beat interval is filtered through clustering, and a heart rate measurement result is obtained based on the corrected inter-beat interval.

Referring to FIG. 7, in the method of measuring a heart rate according to one embodiment of the present disclosure, in step 701, a BCG signal is measured using a non-contact sensor.

That is, in the method of measuring a heart rate according to one embodiment of the present disclosure, a BCG signal is measured using a non-contact sensor from a heart rate measurement target.

In the method of measuring a heart rate according to one embodiment of the present disclosure, in step 702, an inter-beat interval (IBI) may be estimated by applying a window to the BCG signal measured in step 701.

That is, in the method of measuring a heart rate according to one embodiment of the present disclosure, an inter-beat interval, which is a probabilistic fusion estimate, may be estimated by combining the peaks of probability density functions of an auto-correlation estimate, an average magnitude difference function estimate, and a maximum amplitude pair estimate by applying a window to the BCG signal measured in step 701.

In the method of measuring a heart rate according to one embodiment of the present disclosure, in step 703, a confidence value is determined, and an inter-beat interval is filtered based on the determined confidence value to determine a first estimated value.

That is, in the method of measuring a heart rate, a confidence value for the probability values of the inter-beat interval estimated in step 702 may be determined, the estimated inter-beat interval may be filtered by comparing the determined confidence value with a first threshold value, and a first estimated value may be determined.

For example, a confidence value may be determined based on a difference between a maximum probability peak value in the probability values of an inter-beat interval and an average value of other peak values.

In the method of measuring a heart rate according to one embodiment of the present disclosure, in step 704, a repetition degree indicating that identical beat values are successively estimated for the estimated inter-beat interval may be determined, the estimated inter-beat interval may be filtered by comparing the determined repetition degree with a second threshold value, and a second estimated value may be determined.

That is, in the method of measuring a heart rate according to one embodiment of the present disclosure, a repetition degree may be determined by configuring a set of values in which identical beat values are successively repeated for a preset time. When a repetition degree determined from the estimated inter-beat interval is greater than or equal to a second threshold value, a second estimated value may be determined from the estimated inter-beat interval. When a repetition degree determined from the estimated inter-beat interval is less than the second threshold value, the estimated inter-beat interval may be estimated as noise and excluded.

In the method of measuring a heart rate according to one embodiment of the present disclosure, in step 705, a third estimated value may be determined based on the first and second estimated values, and a heart rate may be output based on an inter-beat interval based on the determined third estimated value.

That is, in the method of measuring a heart rate according to one embodiment of the present disclosure, an inter-beat interval corresponding to a third filtering value satisfying that a confidence value exceeds a first threshold value based on a first filtering value in an estimated inter-beat interval and a repetition degree is greater than or equal to a second threshold value based on a second filtering value may be output. The output inter-beat interval may be converted into a heart rate, and the converted heart rate may be output.

Therefore, the present disclosure may provide accurate heart rate measurement results under various environments based on a non-contact sensor by filtering and correcting inter-beat intervals estimated from BCG signals using a confidence value and a repetition degree.

The present disclosure can provide a heart rate measurement apparatus for estimating the inter-beat interval (IBI) of a ballistocardiograph (BCG) signal measured using a non-contact sensor, filtering and correcting inaccurate information in the inter-beat interval estimated through clustering, and outputting a heart rate measurement result based on the filtered and corrected inter-beat interval and a heart rate measurement method thereof.

The present disclosure can increase heart rate measurement accuracy and secure the convenience of a user using a non-contact sensor by determining a confidence value and a repetition degree from an inter-beat interval estimated from a BCG signal and filtering and correcting unnecessary information corresponding to noise by comparing the determined confidence value and repetition degree with threshold values.

The present disclosure can provide accurate heart rate measurement results under various environments based on a non-contact sensor by filtering and correcting inter-beat intervals estimated from BCG signals using a confidence value and a repetition degree.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of executing and responding to instructions. The processing device may execute an operating system (OS) and one or more software applications executing on the operating system. In addition, the processing device may access, store, manipulate, process, and generate data in response to execution of the software. For ease of understanding, the processing apparatus may be described as being used singly, but those skilled in the art will recognize that the processing apparatus may include a plurality of processing elements and/or a plurality of types of processing elements. For example, the processing apparatus may include a plurality of processors or one processor and one controller. Other processing configurations, such as a parallel processor, are also possible.

The software may include computer programs, code, instructions, or a combination of one or more of the foregoing, configure the processing apparatus to operate as desired, or command the processing apparatus, either independently or collectively. In order to be interpreted by a processing device or to provide instructions or data to a processing device, the software and/or data may be embodied permanently or temporarily in any type of a machine, a component, a physical device, a virtual device, a computer storage medium or device, or a transmission signal wave. The software may be distributed over a networked computer system and stored or executed in a distributed manner. The software and data may be stored in one or more computer-readable recording media.

Although the present disclosure has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

What is claimed is:

1. An apparatus for measuring a heart rate, the apparatus implemented in a combination of hardware and software and comprising:

a memory configured to store computer-readable instructions; and one or more processors configured to execute the instructions to:

measure, by using a non-contact sensor placed in a surface a heart rate measurement target is on while avoiding direct contact with the heart rate measurement target, a ballistocardiograph (BCG) signal from the heart rate measurement target, estimate an inter-beat interval (IBI) by applying a window to the measured BCG signal, determine a confidence value for probability values of the estimated inter-beat interval, filter the estimated inter-beat interval by comparing the determined confidence value with a first threshold value, and determine a first estimated value, determine a repetition degree indicating that identical beat values are successively estimated for the estimated inter-beat interval, filter the estimated inter-beat interval by comparing the determined repetition degree with a second threshold value, and determine a second estimated value, and determine a third estimated value for the estimated inter-beat interval based on the determined first and second estimated values and output a heart rate based on the determined third estimated value, wherein the one or more processors are configured to execute the instructions to:

obtain an auto-correlation estimate, an average magnitude difference function (AMDF) estimate, and a maximum amplitude pair (MAP) estimate from the BCG signal, combine peaks of probability density functions of the auto-correlation estimate, the average magnitude difference function (AMDF) estimate, and the maximum amplitude pair (MAP) estimate to determine a probabilistic fusion estimate, and estimate the inter-beat interval based on a peak of a probability density function of the probabilistic fusion estimate, wherein the one or more processors are configured to execute the instructions to:

obtain the auto-correlation estimate while a probability value is changed based on autocorrelation on a right side of a portion designated as the window and a left side of the portion designated as the window, obtain the average magnitude difference function (AMDF) estimate by taking a reciprocal number of a probability value according to a difference between the right side of the portion designated as the window and the left side of the portion designated as the window, and obtain the maximum amplitude pair (MAP) estimate as a probability value when two peaks exist in a section spaced apart by a window size from the portion designated as the window, and wherein the one or more processors are configured to execute the instructions to:

output an inter-beat interval corresponding to the third estimated value satisfying that the confidence value exceeds the first threshold value based on the first estimated value and the repetition degree is greater than or equal to the second threshold value based on the second estimated value, convert the output inter-beat interval into the heart rate, and output the converted heart rate.

2. The apparatus according to claim 1, wherein the one or more processors are configured to execute the instructions to determine the confidence value based on a difference between a maximum probability peak value among the probability values and an average value of other peak values excluding the maximum probability peak value among the probability values.

3. The apparatus according to claim 2, wherein, when the confidence value exceeds the first threshold value, the one or more processors are configured to execute the instructions to determine the first estimated value from the estimated inter-beat interval, and when the confidence value is less than or equal to the first threshold value, the one or more processors are configured to execute the instructions to estimate the estimated inter-beat interval as noise and exclude the estimated inter-beat interval.

4. The apparatus according to claim 1, wherein the one or more processors are configured to execute the instructions to determine the repetition degree by configuring a set of values in which the identical beat values are successively repeated for a preset time.

5. The apparatus according to claim 4, wherein, when the repetition degree determined from the estimated inter-beat interval is greater than or equal to the second threshold value, the one or more processors are configured to execute the instructions to determine the second estimated value from the estimated inter-beat interval, and when the repetition degree determined from the estimated inter-beat interval is less than the second threshold value, the one or more processors are configured to execute the instructions to estimate the estimated inter-beat interval as noise and exclude the estimated inter-beat interval.

6. A processor-implemented method of measuring a heart rate by an apparatus implemented in a combination of hardware and software and comprising a memory configured to store computer-readable instructions, and one or more processors configured to execute the computer-readable instructions to perform the processor-implemented method, the method comprising:

measuring, by the one or more processors, by using a non-contact sensor placed in a surface a heart rate measurement target is on while avoiding direct contact with the heart rate measurement target, a ballistocardiograph (BCG) signal from the heart rate measurement target;

estimating, by the one or more processors, an inter-beat interval (IBI) by applying a window to the measured BCG signal;

determining, by the one or more processors, a confidence value for probability values of the estimated inter-beat interval, filtering, by the one or more processors, the estimated inter-beat interval by comparing the determined confidence value with a first threshold value, and determining, by the one or more processors, a first estimated value;

determining, by the one or more processors, a repetition degree indicating that identical beat values are successively estimated for the estimated inter-beat interval, filtering, by the one or more processors, the estimated inter-beat interval by comparing the determined repetition degree with a second threshold value, and determining, by the one or more processors, a second estimated value; and determining, by the one or more processors, a third estimated value for the estimated inter-beat interval based on the determined first and second estimated values and outputting, by the one or more processors, a heart rate based on the determined third estimated value, wherein the estimating of the inter-beat interval comprises:

obtaining an auto-correlation estimate, an average magnitude difference function (AMDF) estimate, and a maximum amplitude pair (MAP) estimate from the BCG signal, combining peaks of probability density functions of the auto-correlation estimate, the average magnitude difference function (AMDF) estimate, and the maximum amplitude pair (MAP) estimate to determine a probabilistic fusion estimate, and estimating the inter-beat interval based on a peak of a probability density function of the probabilistic fusion estimate, wherein the obtaining of the auto-correlation estimate, the average magnitude difference function (AMDF) estimate, and the maximum amplitude pair (MAP) estimate from the BCG signal comprises:

obtaining the auto-correlation estimate while a probability value is changed based on autocorrelation on a right side of a portion designated as the window and a left side of the portion designated as the window, obtaining the average magnitude difference function (AMDF) estimate by taking a reciprocal number of a probability value according to a difference between the right side of the portion designated as the window and the left side of the portion designated as the window, and obtaining the maximum amplitude pair (MAP) estimate as a probability value when two peaks exist in a section spaced apart by a window size from the portion designated as the window, and wherein the outputting of the heart rate comprises:

outputting the inter-beat interval corresponding to the third estimated value satisfying that the confidence value exceeds the first threshold value based on the first estimated value and the repetition degree is greater than or equal to the second threshold value based on the second estimated value, converting the output inter-beat interval into the heart rate, and outputting the converted heart rate.

7. The method according to claim 6, wherein the determining of the first estimated value comprises determining the confidence value based on a difference between a maximum probability peak value among the probability values and an average value of other peak values excluding the maximum probability peak value among the probability values;

determining the first estimated value from the estimated inter-beat interval when the confidence value exceeds the first threshold value; and estimating the estimated inter-beat interval as noise and excluding the estimated inter-beat interval when the confidence value is less than or equal to the first threshold value.

8. The method according to claim 6, wherein the determining of the second estimated value comprises determining the repetition degree by configuring a set of values in which the identical beat values are successively repeated for a preset time;

determining the second estimated value from the estimated inter-beat interval when the repetition degree determined from the estimated inter-beat interval is greater than or equal to the second threshold value; and estimating the estimated inter-beat interval as noise and excluding the estimated inter-beat interval when the repetition degree determined from the estimated inter-beat interval is less than the second threshold value.

* * * * *